US007846115B2

(12) United States Patent  (10) Patent No.: US 7,846,115 B2
Seligman et al. (45) Date of Patent: *Dec. 7, 2010

(54) MOTION CONTROLLING HINGE FOR ORTHOPEDIC BRACE

(75) Inventors: Scott Seligman, San Marcos, CA (US); Michael Strobel, Straubing (DE)

(73) Assignee: DJO, LLC, Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,997

(22) Filed: Apr. 10, 2009

(65) Prior Publication Data

US 2009/0198161 A1 Aug. 6, 2009

Related U.S. Application Data

(63) Continuation of application No. 11/675,014, filed on Feb. 14, 2007, now Pat. No. 7,534,217, which is a continuation of application No. 10/355,486, filed on Jan. 30, 2003, now Pat. No. 7,192,407.

(51) Int. Cl.
*A61F 5/00* (2006.01)
(52) U.S. Cl. ............................. 602/16; 602/23; 602/27
(58) Field of Classification Search ..................... 602/5, 602/16, 20, 23, 26–27; 128/882
See application file for complete search history.

(56) References Cited

U.S. PATENT DOCUMENTS

| 401,933 | A | | 4/1889 | De Camp |
| 2,883,982 | A | | 4/1959 | Rainey |
| 3,473,527 | A | | 10/1969 | Spiro |
| 4,366,813 | A | | 1/1983 | Nelson |
| 4,370,977 | A | * | 2/1983 | Mauldin et al. ............... 602/16 |
| 4,817,588 | A | | 4/1989 | Bledsoe |
| 4,838,251 | A | | 6/1989 | Chignon et al. |
| 4,865,024 | A | | 9/1989 | Hensley et al. |
| 5,038,765 | A | | 8/1991 | Young et al. |
| 5,261,871 | A | | 11/1993 | Greenfield |

(Continued)

FOREIGN PATENT DOCUMENTS

DE 19904554 8/2000

(Continued)

OTHER PUBLICATIONS

Office Action issued Sep. 9, 2009 in Japanese Application No. 2006-503218.

*Primary Examiner*—Michael A. Brown
(74) *Attorney, Agent, or Firm*—Ropes & Gray LLP

(57) ABSTRACT

A motion controlling hinge for an orthopedic brace is provided. The hinge includes an actuator secured to one arm, and at least one spring member. As the arm with the actuator pivots in a first direction, at a predetermined flexion angle the actuator applies a force to the spring member, causing the spring member to flex. The spring member exerts a force on the actuator tending to bias the actuator away from the spring member, and tending to bias the arm in a second direction opposite the first direction. A movable fulcrum enables adjustment of a force exerted by the spring member on the actuator. A variety of differently sized adapters are securable to the actuator. The size of the adapter determines the flexion angle at which the spring member first exerts force on the actuator.

20 Claims, 13 Drawing Sheets

U.S. PATENT DOCUMENTS

| | | | |
|---|---|---|---|
| 5,358,469 A | 10/1994 | Patchel et al. | |
| 5,419,754 A | 5/1995 | Hutchins et al. | |
| 5,437,611 A * | 8/1995 | Stern | 602/16 |
| 5,437,619 A | 8/1995 | Malewicz et al. | |
| 5,443,444 A | 8/1995 | Pruyssers | |
| 5,472,412 A | 12/1995 | Knoth | |
| 5,658,241 A | 8/1997 | Deharde et al. | |
| 5,676,640 A | 10/1997 | Biedermann et al. | |
| 5,749,840 A | 5/1998 | Mitchell et al. | |
| 5,873,847 A | 2/1999 | Bennett et al. | |
| 5,954,677 A | 9/1999 | Albrecht et al. | |
| 5,980,435 A * | 11/1999 | Joutras et al. | 482/114 |
| 6,004,283 A * | 12/1999 | Young | 602/16 |
| 6,074,355 A | 6/2000 | Bartlett | |
| 6,129,690 A | 10/2000 | Hamlin et al. | |
| RE37,209 E | 6/2001 | Hensley et al. | |
| 6,387,066 B1 | 5/2002 | Whiteside | |
| 6,402,711 B1 | 6/2002 | Nauert | |
| 7,192,407 B2 * | 3/2007 | Seligman et al. | 602/16 |
| 7,534,217 B2 * | 5/2009 | Seligman et al. | 602/16 |

FOREIGN PATENT DOCUMENTS

| | | |
|---|---|---|
| EP | 0262758 | 4/1988 |
| WO | WO 86/00228 | 7/1986 |
| WO | WO 90/04371 | 5/1990 |

\* cited by examiner

MOTION CONTROLLING HINGE FOR ORTHOPEDIC BRACE

CROSS REFERENCE TO RELATED APPLICATIONS

This application is a continuation of U.S. patent application Ser. No. 11/675,014, filed Feb. 14, 2007, which is a continuation of U.S. patent application Ser. No. 10/355,486, filed Jan. 30, 2003, now U.S. Pat. No. 7,192,407, the entire contents of which are hereby incorporated by reference.

BACKGROUND OF THE INVENTION

1. Field of the Invention

The present invention relates to orthopedic bracing. More particularly, the present motion controlling hinge for an orthopedic brace provides resistance to joint extension, with the resistance beginning at a predetermined angle and increasing as the joint extends further.

2. Description of the Related Art

The quadriceps muscles serve as an anterior cruciate ligament (ACL) antagonist that strain the ACL, particularly at smaller knee flexion angles. At knee flexion angles less than 60°, a component of the quadriceps force acts in the anterior direction. Knee structures, primarily the ACL, resist this anterior component. Thus, quadriceps contractions at small flexion angles place strain on the ACL. This strain may be responsible for many ACL injuries. For patients who have recently undergone ACL reconstruction, this strain can cause permanent stretching of the ACL graft, which can in turn create knee instability that could lead to injury of other structures (e.g. meniscus), or to degenerative changes within the joint. In some cases, the patient must undergo a second invasive procedure to reduce the instability.

Because of the risk of ACL damage at small flexion angles, physicians commonly recommend avoiding quadriceps contractions at small flexion angles. However, people often have difficulty avoiding small flexion angles during normal activities. Furthermore, movement and activity are important to promoting healing and reducing detrimental effects of ACL reconstruction. Therefore, a knee brace that allows patients to avoid quadriceps contractions at small flexion angles would be of great benefit to ACL reconstruction patients or to people who suffer from ACL deficiencies.

One type of knee brace that allows patients to avoid small flexion angles is a brace having extension stops, such that the wearer cannot extend his or her knee past a particular flexion angle. For example, U.S. Pat. No. 4,732,143 to Kausek et al. provides an extension stop removably mountable on a polycentric hinge. The stop limits the forward pivotal rotation of a pair of rigid arms pivotally connected by the hinge. The hinge includes a pair of rigid arms connected at spaced-apart pivotal connections between a pair of parallel face plates. Intermeshing gear teeth on the mating ends of the arms cause simultaneous pivotal action of both arms about their pivotal connections with the plates. The extension stop is a C-shaped plastic body that is attachable along one of the face plates. The stop includes a resilient clip for attaching the stop to one of the face plates. The stop further includes an extension block positionable between the mating ends of the arms to limit the forward rotation of the arms. The extension stop is made of a strong, lightweight plastic. Differently sized block means are provided to allow the user to select the limit of extension.

A brace such as the one described in Kausek et al. halts the wearer's knee extension at a particular flexion angle. A patient wearing such a brace experiences a jarring at maximum extension as the brace comes to a sudden halt. Many patients may find this jarring uncomfortable, and the jarring may cause many patients to fail to comply with the rehabilitation guidelines set by their physicians. A joint brace that provides a cushioned stop at full joint extension and/or full joint flexion can help to reduce or eliminate uncomfortable jarring. The brace might make patients feel safer and more confident, which may lead to better patient compliance with rehabilitation programs and speedier recovery times.

Athletes frequently leap off of the ground during various athletic activities. These athletes preferably land with their knees slightly bent. The impact causes their knees to bend further as the quadriceps muscles contract to provide a force that decelerates and eventually halts knee flexion. The knees thus absorb the impact forces and prevent these forces from damaging fragile bones and other joints.

Occasionally, however, athletes do not flex their knees while they are in the air. Studies have shown that female athletes tend not to flex their knees as much as male athletes do when landing after a jump. When a person lands with his or her knees fully extended, the knees do not bend. Instead, all of the impact forces are absorbed by the athlete's bones and/or joints. Such jarring impacts frequently cause injuries. If an athlete were to wear knee braces that included a stop or a cushion that prevented full knee extension, or that biased the knee joint away from full extension, the braces would force the athlete to flex his or her knees while airborne. The athlete would thus always land on flexed knees and would be less likely to injure himself or herself.

Several joint braces include hinges that either prevent full joint extension, or provide a cushioned stop at full joint extension. U.S. Pat. No. RE37,209 to Hensley et al. provides an extension deceleration orthosis. The orthosis performs the function of those ligaments that control joint motion, and provides added anteroposterior joint stability. The orthosis comprises a lightweight, external spring assembly, upper and lower elongated arms, and a centric or polycentric fulcrum. The orthosis is adjustable for its range of motion, adaptable for use on many different style orthoses, and includes variable strength to suit corrective, preventive, anthropomorphic, environmental, and usage requirements. The orthosis includes means for mechanically dampening a limb's angular velocity on extension to prevent hyperextension. The orthosis further includes means for accelerating the limb's angular velocity on flexion to enable quicker, smoother, less stressful motion. In one embodiment, spring rods are assembled medially and laterally to conventional pairs of elongated orthotic brace arms. The spring rods span the joint fulcrum point by serpentinely engaging roller posts. The assemblage thus decelerates the limb during the last 15 to 20 degrees of extension, preventing the arms from striking a stop, which would create a risk of hyperextension. The assemblage also uses the stored energy of the spring to facilitate limb flexion.

U.S. Pat. No. 6,074,355 to Bartlett provides a knee brace having three point fixation and including a pair of first arm members positioned on opposite sides of the knee joint. The lower leg brace member has a pair of second arm members oriented and positionable on opposite sides of the knee joint. The rigid thigh member and lower leg member are secured to the wearer's leg by means of a flexible strap extending around the back of the leg and adjustably attached thereto. The mating ends of the arms are connected by a pair of parallel spaced-apart face plates forming polycentric hinges that permit the mating ends of the arms to pivot about the connections. Various forms of extension cushions are provided to limit the proximity of the mating ends to one another to thereby limit the forward movement of the arms.

None of these braces provides the ability to adjust a magnitude of a force that restrains hinge motion without the necessity of interchanging hinge parts. Further none of these braces provides the advantageous combination of easy adjustability of a magnitude of a force that restrains hinge motion, and easy adjustability of an angle at which the hinge motion controlling force is applied. Therefore, a hinge for an orthopedic brace that provided these advantages would be of great benefit to wearers of orthopedic braces.

SUMMARY OF THE INVENTION

The preferred embodiments of the motion controlling hinge for orthopedic brace have several features, no single one of which is solely responsible for their desirable attributes. Without limiting the scope of this invention as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include easy adjustability of a magnitude of a force that restrains hinge motion, and easy adjustability of an angle at which the hinge motion controlling force is applied.

A preferred embodiment of the hinge for orthopedic brace comprises a hinge plate, a spring member, and first and second arms pivotably secured to the hinge plate. An actuator is secured to the second arm. As the arms pivot in a first direction such that an angle between them increases, once the arms reach a desired extension angle, the spring member exerts a force on the actuator tending to bias the second arm in a second direction opposite the first direction.

Another preferred embodiment of the hinge for orthopedic brace comprises an orthopedic brace including a hinge. The hinge comprises a hinge plate, a spring member and first and second arms pivotably secured to the hinge plate. An actuator is secured to the second arm. As the brace pivots toward full extension, the spring member exerts a force on the actuator tending to bias the brace away from full extension.

Another preferred embodiment of the hinge for orthopedic brace comprises a hinge plate, a leaf spring, and first and second arms pivotably secured to the hinge plate. An actuator is secured to the second arm. As the second arm pivots in a first direction, the actuator contacts the leaf spring, causing the leaf spring to flex such that the leaf spring exerts a force on the actuator tending to bias the actuator away from the leaf spring, and tending to bias the second arm in a second direction opposite the first direction.

Another preferred embodiment of the hinge for orthopedic brace comprises a hinge plate, a leaf spring shaped substantially as a flat bar, and first and second arms pivotably secured to the hinge plate. As the arms pivot toward a first configuration in which an angle between them approaches 180°, the leaf spring exerts a force on the second arm tending to bias the second arm away from the first configuration.

Another preferred embodiment of the hinge for orthopedic brace comprises a resistance member for providing resistance to motion of the hinge in a first direction within a predetermined range of motion of the hinge, and an adjustment member adapted to apply a force on the resistance member for adjusting an amount of the resistance provided by the resistance member. When the adjustment member is located in a first location relative to the resistance member, the resistance provided by the resistance member has a first magnitude. When the adjustment member is located in a second location relative to the resistance member, the resistance provided by the resistance member has a second magnitude that is different from the first magnitude.

BRIEF DESCRIPTION OF THE DRAWINGS

The preferred embodiments of the motion controlling hinge for orthopedic brace, illustrating its features, will now be discussed in detail. These embodiments depict the novel and non-obvious hinge shown in the accompanying drawings, which are for illustrative purposes only. These drawings include the following figures, in which like numerals indicate like parts.

DETAILED DESCRIPTION OF THE PREFERRED EMBODIMENTS

Figure 1:
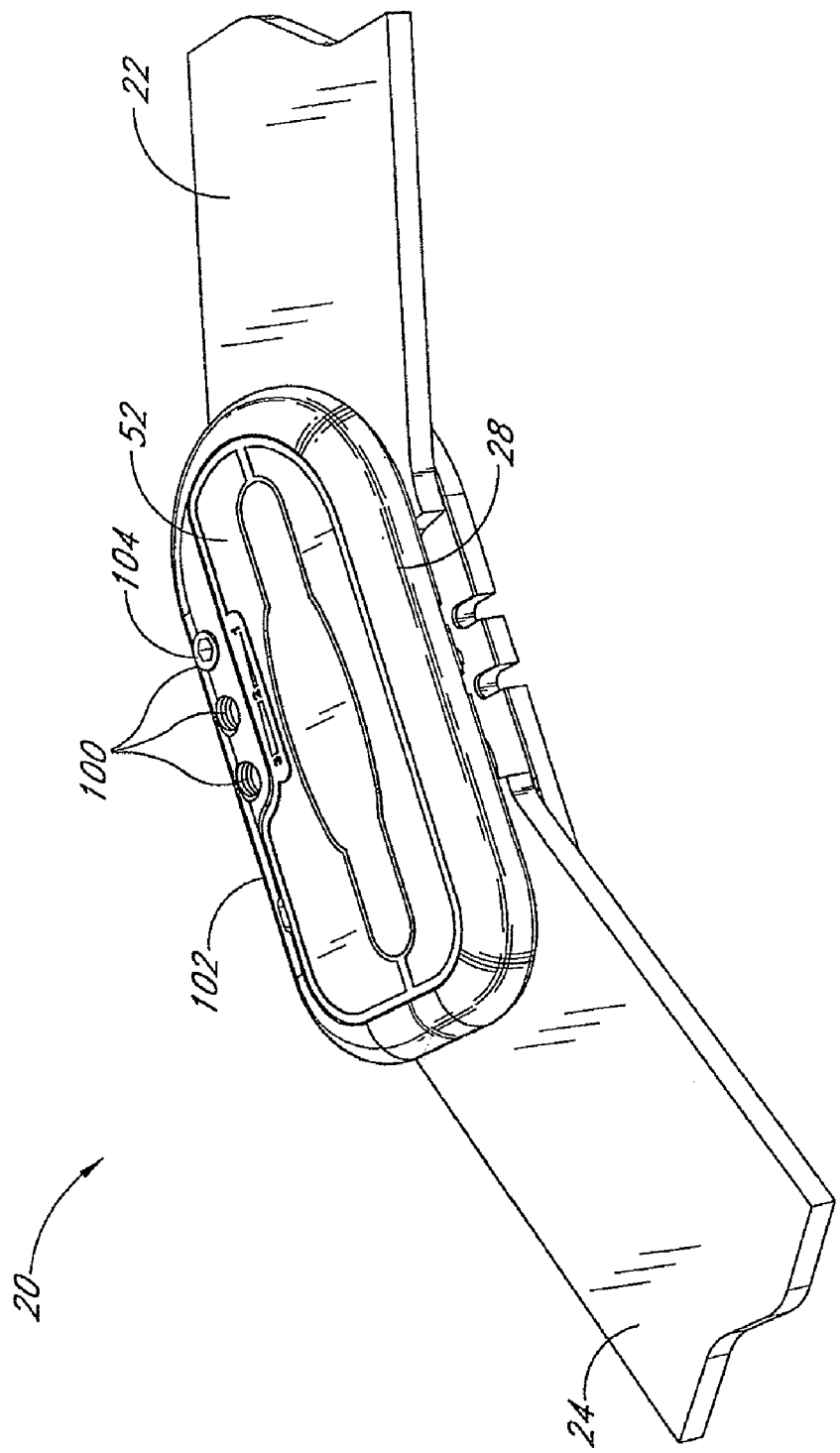
FIG. 1 is a top-rear perspective view of a preferred embodiment of the motion controlling hinge for orthopedic brace according to the present invention.
Figure 2:
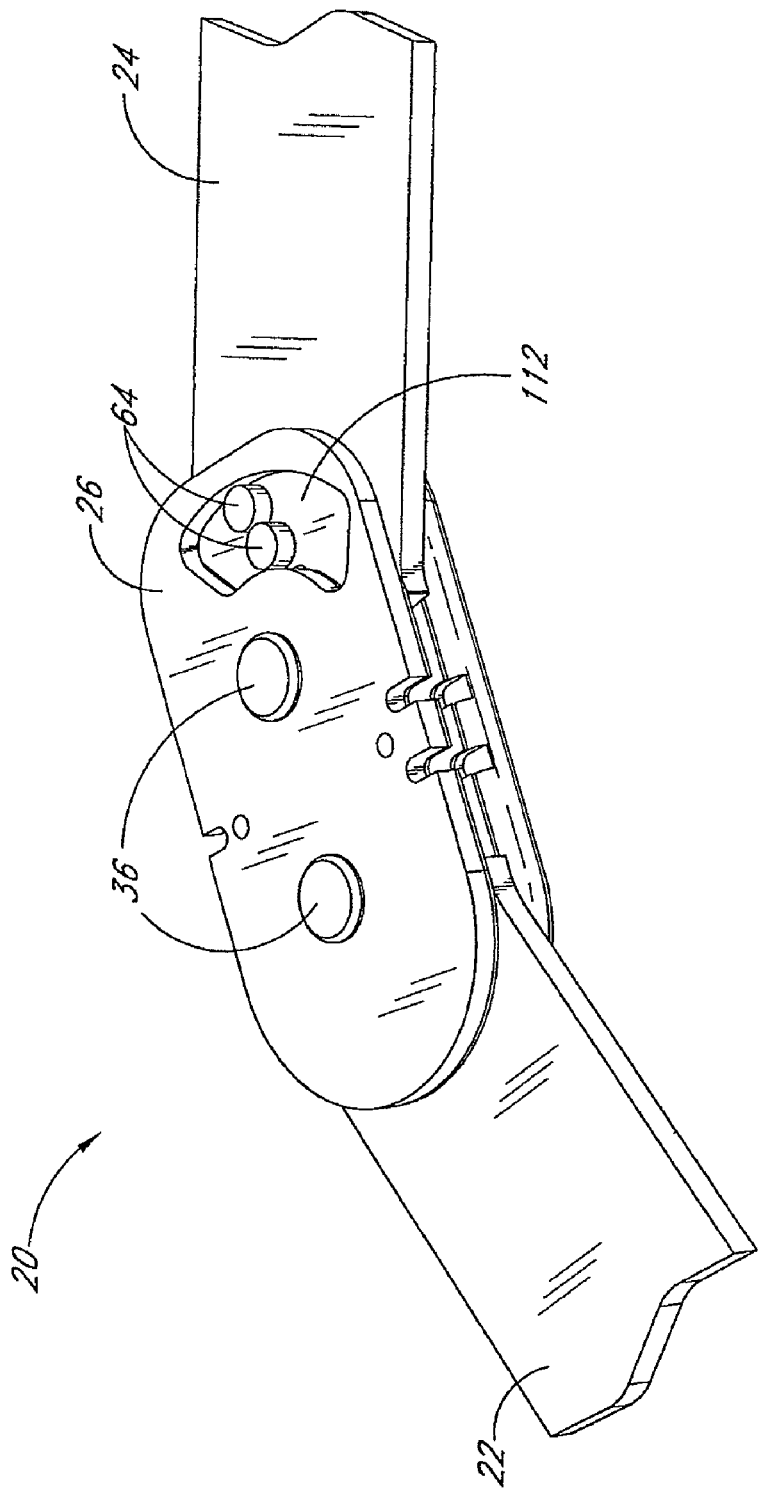
FIG. 2 is a bottom-rear perspective view of the hinge of FIG. 1.
Figure 3:
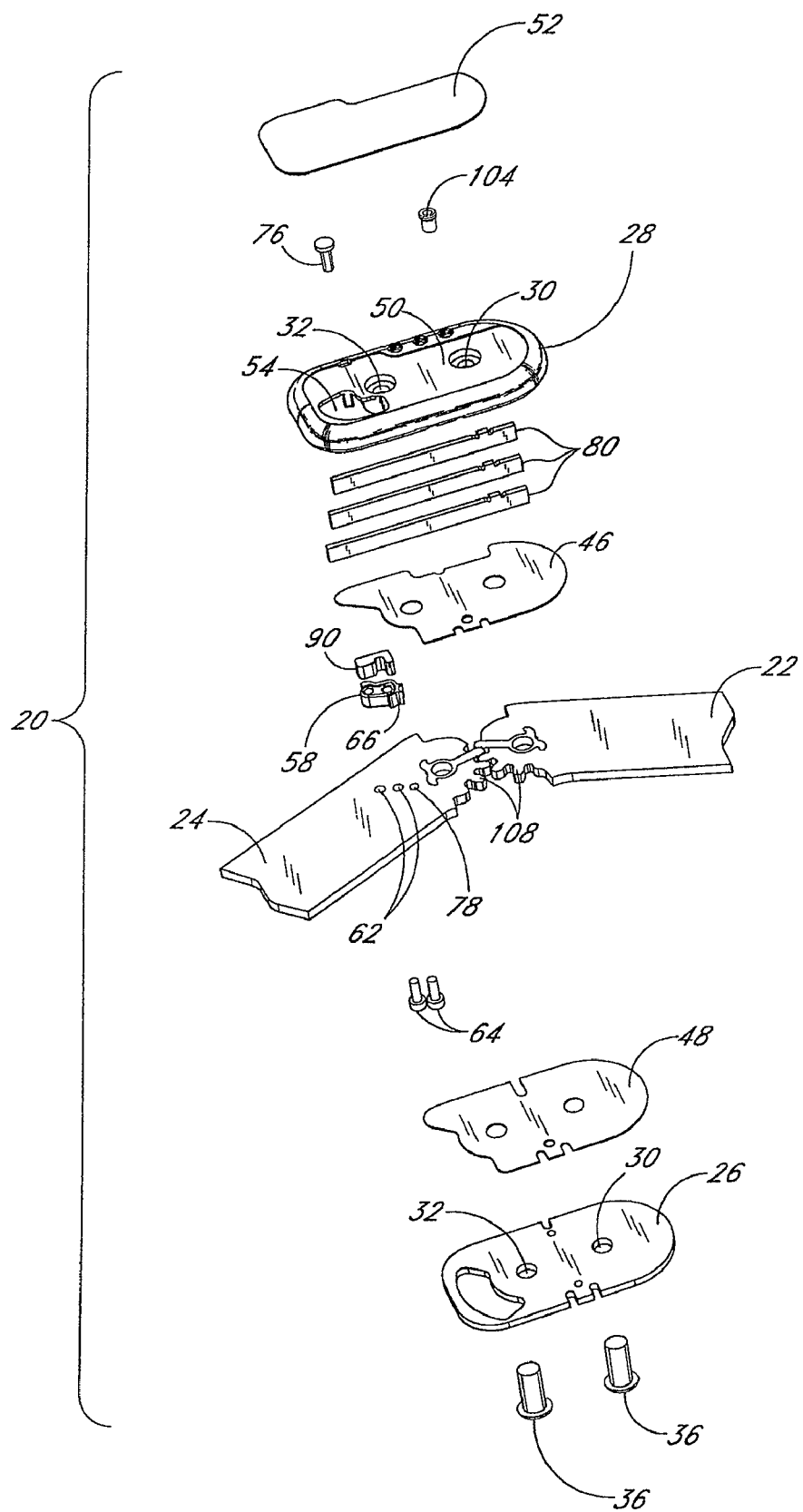
FIG. 3 is an exploded top-rear perspective view of the hinge of FIG. 1.
Figure 4:
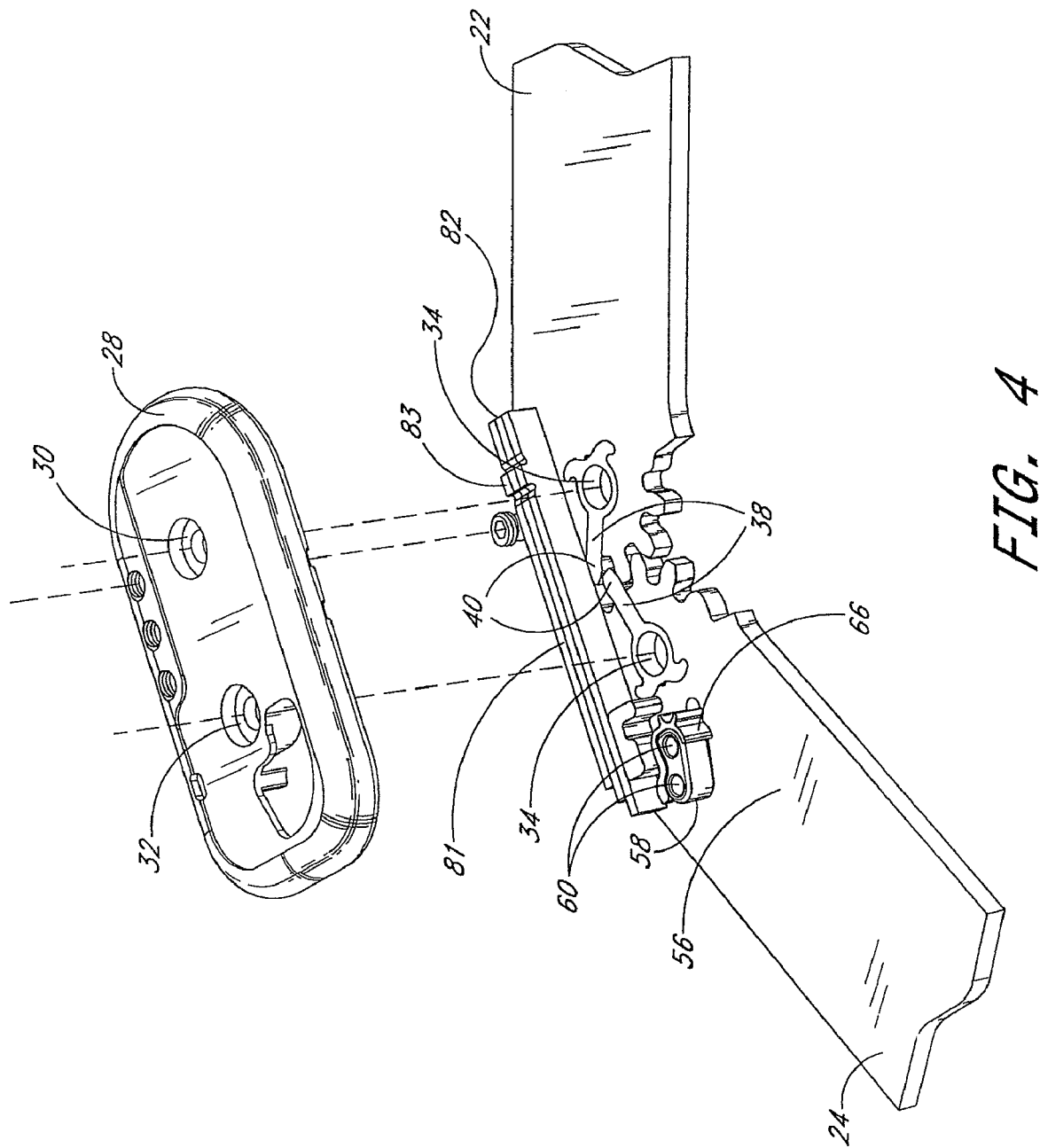
FIG. 4 is a partially exploded top-rear perspective view of the actuator, adapter, bumper, springs, fulcrum, arms and outer hinge plate of the hinge of FIG. 1.

FIGS. 1 and 2 illustrate the exterior of the present motion controlling hinge 20 for orthopedic brace. FIG. 3 illustrates, in an exploded view, the interior components of the hinge 20. The hinge 20 comprises a first rigid arm 22 and a second rigid arm 24 pivotably secured between an inner hinge plate 26 (FIGS. 2 and 3) and an outer hinge plate 28 (FIGS. 1 and 3). With reference to FIGS. 3 and 4, each hinge plate 26, 28 preferably includes a first pivot aperture 30 and a second pivot aperture 32 spaced from the first pivot aperture 30. Each arm 22, 24 preferably includes a pivot aperture 34 near a mating end thereof. As shown in FIGS. 2 and 3, a first fastening member 36, such as a rivet, passes through the first pivot aperture 30 on each hinge plate 26, 28 and through the pivot aperture 34 on the first arm 22, thereby pivotably securing the first arm 22 between the hinge plates 26, 28. A second fastening member 36, such as a rivet, passes through the second pivot aperture 32 on each hinge plate 26, 28 and through the pivot aperture 34 on the second arm 24, thereby pivotably securing the second arm 24 between the hinge plates 26, 28.

In the illustrated embodiment, the pivot aperture 34 on each arm contains a reinforcing insert 38 (FIG. 4). Preferably, the arms 22, 24 are constructed of a relatively inexpensive and lightweight metal, such as aluminum. Such a lightweight metal lowers the overall weight of a brace including the present hinge 20, making the brace more comfortable for the wearer. However, lightweight metals typically do not have sufficient hardness to enable the arms 22, 24 to withstand prolonged use in the present hinge 20. At the pivot apertures 34 in the arms 22, 24, the arms 22, 24 rub against the fastening members 36. Similarly, a first gear tooth 40 (FIG. 4) on each arm 22, 24 rubs against gear teeth on the opposite arm 22, 24. Friction at these contact points tends to wear down the material at the pivot apertures 34 and the first gear teeth 40. Therefore, the reinforcing inserts 38 provide the arms 22, 24 with greater hardness at the points where the arms 22, 24 experience the greatest wear and tear. Those of skill in the art will appreciate that the reinforcing inserts 38 are not necessary to achieve the advantages of the present hinge 20. The reinforcing inserts 38 merely prolong the expected life span of the present hinge 20 while maintaining low weight and low cost.

Figure 16:
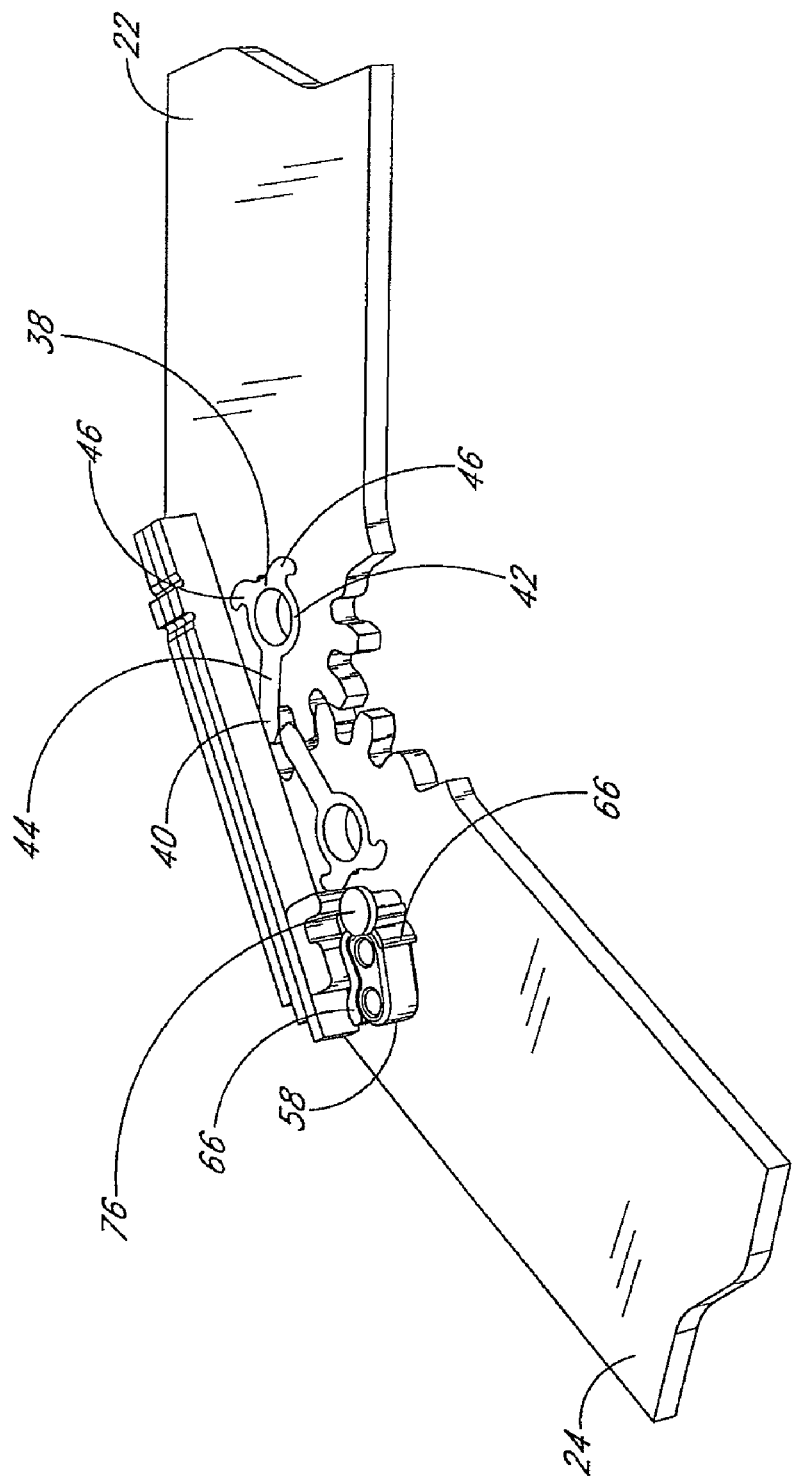
FIG. 16 is a top-rear perspective view of the actuator, adapter, bumper, springs and arms of the hinge of FIG. 1, illustrating the screw that is preferably used to hold the adapter in place on the second arm.

With reference to FIG. 16, the inserts 38 include a ring-shaped portion 42 with an elongate radial protrusion 44. Opposite the radial protrusion 44, the ring-shaped portion 42 includes first and second arcuate protrusions 46 that are substantially tangential to the ring-shaped portion 42. The mating end of each arm 22, 24 preferably includes a cut-out portion having a shape complementary to that of the inserts 38. The inserts 38 may be retained within the cut-out portions by any appropriate means, such as a friction fit or an adhesive. An end of the radial protrusion 44 opposite the ring-shaped portion 44 comprises a first gear tooth 40. The operation of the geared ends of the arms 22, 24 is described in detail below. The inserts 38 are preferably constructed of a material having a high hardness, such as stainless steel. The inserts 38 thus are better able to withstand the wear and tear that the softer arms 22, 24 experience at the pivot apertures 34 and the first gear tooth 40.

The hinge 20 may include a first friction-reducing plate 46 (FIG. 3) sandwiched between the outer hinge plate 28 and the arms 22, 24. The hinge 20 may also include a second friction-reducing plate 48 sandwiched between the inner hinge plate 26 and the arms 22, 24. The friction-reducing plates 46, 48 are preferably constructed of a low-friction material, such as a plastic, TEFLON® or DELRIN®. The friction-reducing plates 46, 48 enable the arms 22, 24 to pivot more easily with respect to the hinge plates 26, 28. Those of skill in the art will appreciate that the hinge 20 need not include the friction-reducing plates 46, 48.

An outer surface 50 of the outer hinge plate 28 preferably includes a removable cosmetic cover 52 (FIGS. 1 and 3) that enhances the outward appearance of the hinge 20. The cover 52 may be secured to the outer hinge plate 28 with, for example, adhesive or an interlocking "snap-fit" engagement. The cover 52 hides from view the pivot apertures 30, 32 and an adapter access opening 54, which is described in detail below.

As shown in FIGS. 3 and 4, an outer surface 56 of the second arm 24 preferably includes an actuator 58 adjacent the pivot aperture 34. In the illustrated embodiment, the actuator 58 comprises an irregularly shaped solid. The actuator 58 includes first and second through-holes 60 (FIG. 4). The first and second through-holes 60 on the actuator 58 align with first and second through-holes 62 (FIG. 3) in the second arm 24. Fastening members 64 (FIG. 3), such as screws or rivets, cooperate with the first and second through-holes 62 in the second arm 24, and with the first and second through-holes 60 in the actuator 58, to secure the actuator 58 to the second arm 24. Those of skill in the art will appreciate that the actuator 58 need not be secured to the second arm 24 with fastening members. For example, the actuator 58 could be bonded to the second arm 24 with adhesive, or it could be welded to the second arm 24. Alternatively, the actuator 58 could be formed integrally with the second arm 24, such as by die-casting. If the actuator 58 is secured to the second arm 24 with fastening members 64, as shown, preferably the inner hinge plate 26 includes a cut-out portion 112 (FIG. 2) so that heads of the fastening members 64 do not interfere with the inner hinge plate 26.

Figure 5:
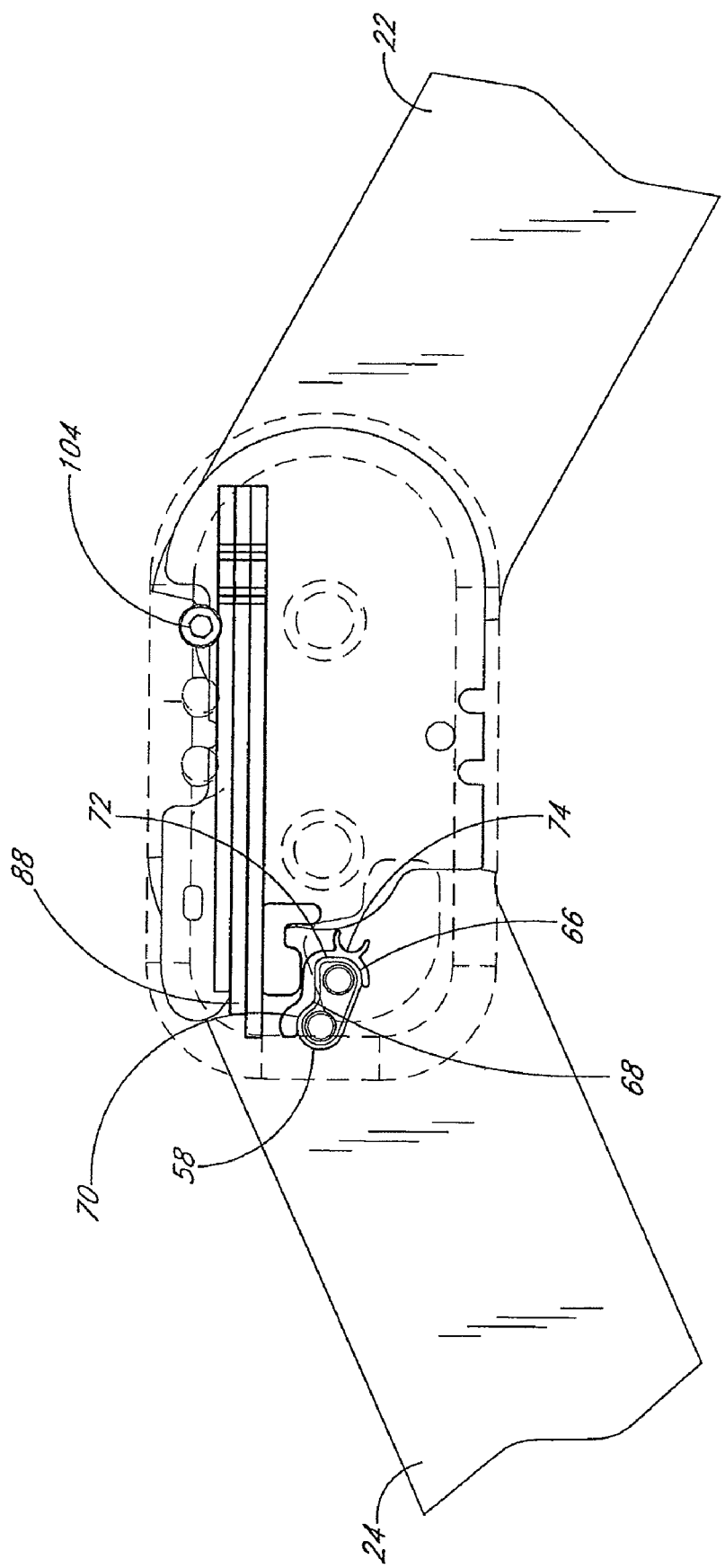
FIG. 5 is a top plan view of the actuator, adapter, bumper, springs, fulcrum, arms and friction plate of the hinge of FIG. 1, illustrating the configuration of these components when the arms are positioned such that the adapter contacts the bumper and the springs are undeflected.

The actuator 58 is preferably constructed of a hard durable material, such as a metal. A preferred metal is stainless steel. An adapter 66 is selectively securable to the actuator 58, as shown in FIGS. 4, 5 and 16. The adapter 66 is substantially J-shaped in top plan aspect (FIG. 5), and includes an interior curved surface 68 that is complementary to an outer side portion 70 of the actuator 58. The adapter 66 thus fits snugly around the actuator 58. The hooked portion 72 of the adapter 66 includes a crescent-shaped flange having a semi-cylindrical concave edge 74. A retaining member 76, such as a screw, engages a third aperture 78 (FIG. 3) in the second arm 24, such that a longitudinal axis of the retaining member 76 is substantially coextensive with a longitudinal axis of the flange concave edge 74. A cylindrical exterior of the retaining member 76 thus cooperates with the concave edge 74 of the flange, thereby firmly holding the adapter 66 in place on the actuator 58.

The adapter 66 is preferably constructed of a hard durable material, such as a metal. A preferred metal is stainless steel. As described below, the adapter 66 enables easy adjustment of a joint flexion angle at which resistance to further flexion begins.

An interior of the outer hinge plate 28 (FIG. 9) houses a plurality of leaf springs 80. In the illustrated embodiment, each leaf spring 80 comprises a flat bar of resilient material. Those of skill in the art will appreciate that the leaf springs 80 need not be shaped as flat bars. For example, the leaf springs 80 could be wedge-shaped (straight tapered bars), or the leaf springs 80 could be arcuate. An upper edge 81 (FIG. 4) of each leaf spring 80 includes a ridge 83 near a first end 82 thereof. A portion (not shown) of the outer hinge plate 28 has a shape that is complementary to the shape of the ridges 83. The ridges 83 nest within this portion of the outer hinge plate 28, and prevent the leaf springs 80 from translating along an axis A (FIGS. 9 and 10) upon which both hinge plate pivot apertures 30, 32 lie.

The leaf springs 80 are preferably constructed of a resilient material that returns to its original shape after the removal of an applied load. A preferred material for the leaf springs 80 is stainless steel. However, those of skill in the art will appreciate that the leaf springs 80 could be constructed of other materials in order to alter the stiffness of the leaf springs 80. For example, less rigid metals or plastics could be used to provide more flexible leaf springs 80, and more rigid metals could be used to provide more stiff leaf springs 80.

In the illustrated embodiment, three leaf springs 80 are provided, and the leaf springs 80 are freely slidable with respect to one another except in the vicinity of the ridges 83. In this vicinity, the nesting of the ridges 83 within the outer hinge plate 28 prevents the leaf springs 80 from sliding with respect to one another. The illustrated leaf springs 80 are of unequal lengths. The innermost leaf spring 80 (the leaf spring 80 that lies closest to the pivot apertures 30, 32) is the longest, and the outermost leaf spring 80 the shortest. This configuration allows the springs 80 greater freedom to flex without interfering with the walls of the outer hinge plate 28. Those of skill in the art will appreciate that the leaf springs 80 need not have unequal lengths.

The three leaf spring configuration provides the advantageous combination of a high amount of extension resistance without significant risk that the leaf springs 80 will break. If the three leaf springs 80 are replaced by a single solid leaf spring 80 having the same stiffness as the three illustrated leaf springs 80, the single leaf spring 80 will be much more likely to break. Nevertheless, those of skill in the art will appreciate that the three leaf springs 80 could be replaced by more or fewer leaf springs 80, including a single leaf spring 80, in order to suit a particular application. Those of skill in the art will also appreciate that the shape, dimensions and/or composition of each leaf spring 80 could be varied to provide desired extension resistance characteristics for the hinge 20. For example, if greater extension resistance is desired, some or all of the leaf springs 80 could be made of a stiffer material. Alternatively, one leaf spring 80 having the same thickness as the three combined leaf springs 80 could be provided. Alternatively, the three springs could be adhered to one another so that they behave essentially as a unitary leaf spring 80.

Figure 9:
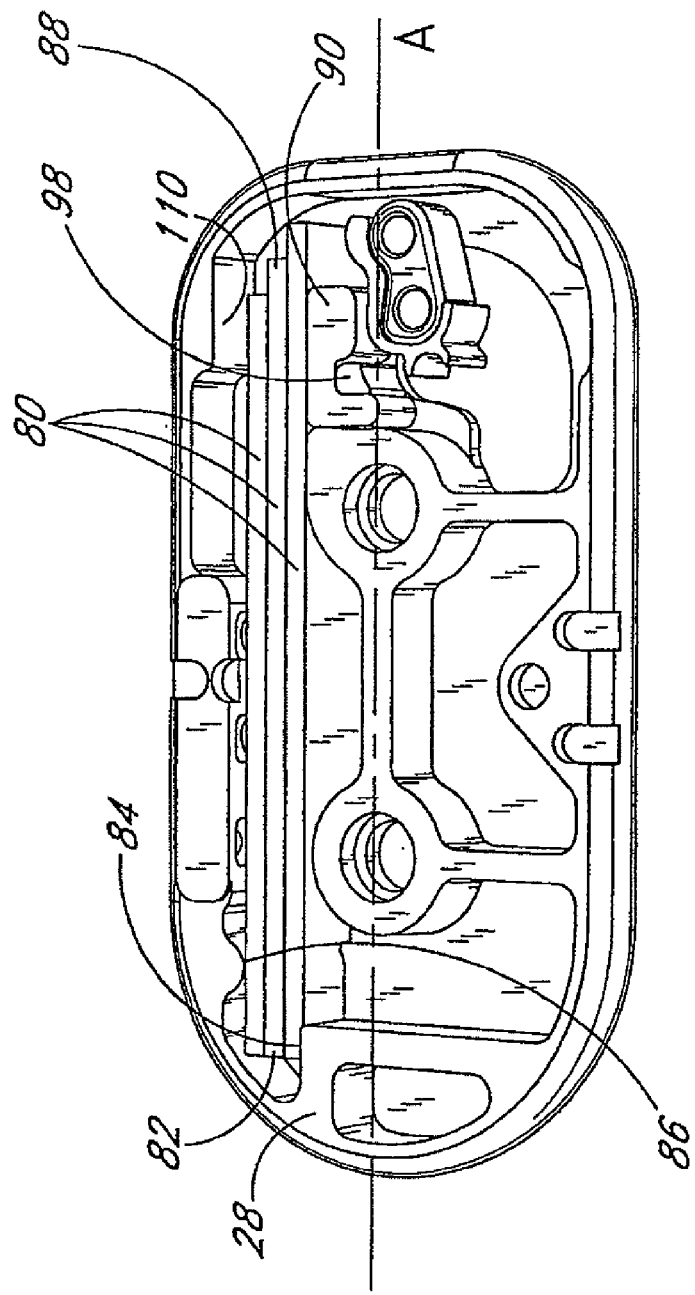
FIG. 9 is a bottom-rear perspective view of the actuator, adapter, bumper, springs and outer hinge plate of the hinge of FIG. 1.
Figure 10:
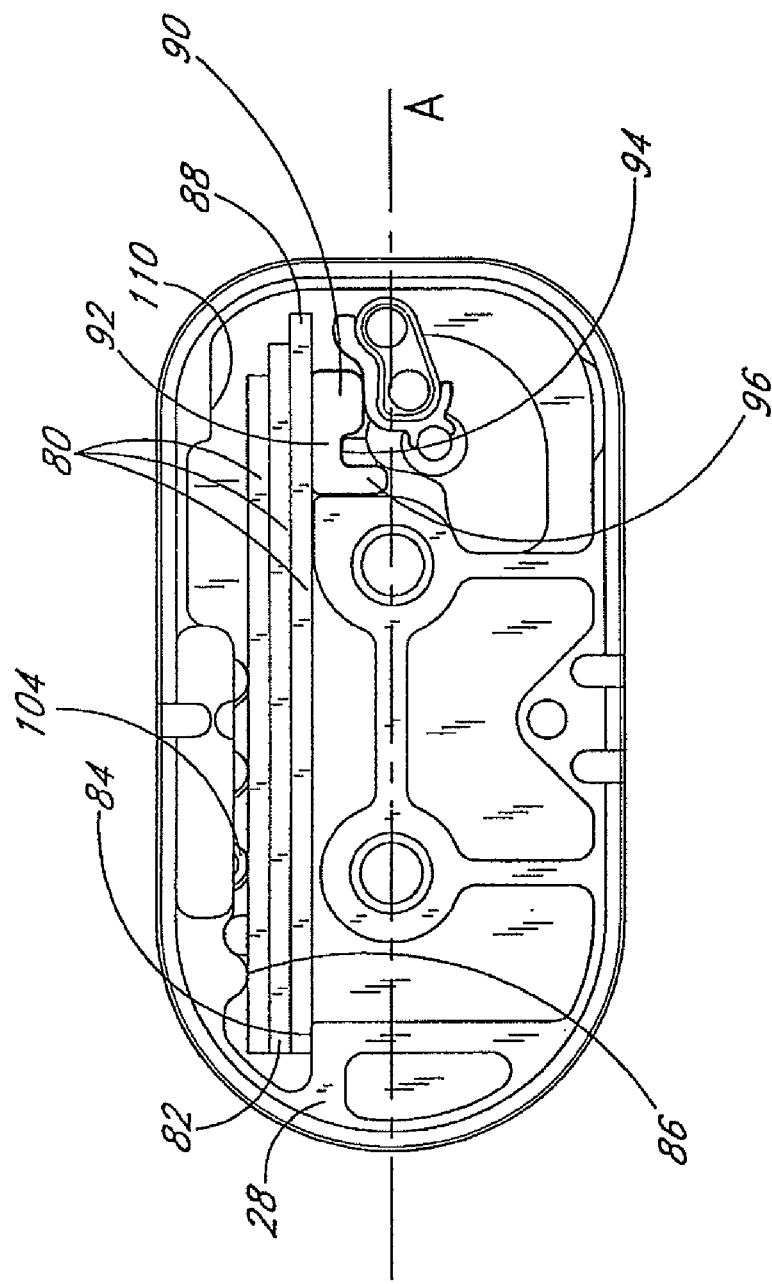
FIG. 10 is a bottom plan view of the actuator, adapter, bumper, springs, fulcrum and outer hinge plate of the hinge of FIG. 1, illustrating the configuration of these components when the arms are positioned such that the adapter contacts the bumper and the springs are undeflected.

With reference to FIGS. 9 and 10, the first end 82 of each leaf spring 80 is constrained by a first wall 84 of the outer hinge plate 28 against translation toward the axis A. A second wall 86 of the outer hinge plate 28 constrains each leaf spring 80, at a point adjacent the first end 82 of each, against translation away from the axis A. Second ends 88 of the leaf springs 80 are free to translate away from the axis A. The leaf springs 80 are thus analogous to cantilevered beams.

The outer hinge plate 28 houses a bumper 90, which is substantially L-shaped in plan aspect (FIG. 10). The bumper 90 is preferably constructed of a deformable but resilient material that provides some cushioning. Preferred materials for the bumper 90 include urethane, rubber and plastic. The bumper 90 provides a cushion between the adapter 66 and the leaf springs 80, which reduces any sound made when the adapter 66 contacts the leaf springs 80, as described below. Those of skill in the art will appreciate that the bumper 90 is not necessary to achieve the advantages of the present hinge 20. The adapter 66 may contact the leaf springs 80 directly. Alternatively, if the adapter 66 were removed completely, the actuator 58 may contact the leaf springs 80 directly.

An upright portion 92 of the bumper 90 includes a flat indentation 94 adjacent an interior corner where the upright portion 92 meets the base portion 96 of the bumper 90. The flat indentation 94 receives a post 98 (FIG. 9) that protrudes from the outer hinge plate 28. The post 98 retains the bumper 90 in its rest position, and guides the bumper 90 back to the rest position, as described below.

The outer hinge plate 28 includes a plurality of apertures 100 adjacent a front edge 102 thereof. In the illustrated embodiment, three apertures 100 are provided, and all the apertures 100 include internal threads. Those of skill in the art will appreciate that more or fewer apertures 100 could be provided to suit a particular application, and that the apertures 100 need not be threaded. A longitudinal axis of each aperture is substantially perpendicular to a plane defined by the outer hinge plate 28. When viewed in plan aspect (FIG. 15), centers of the apertures 100 are collinear.

Figure 15:
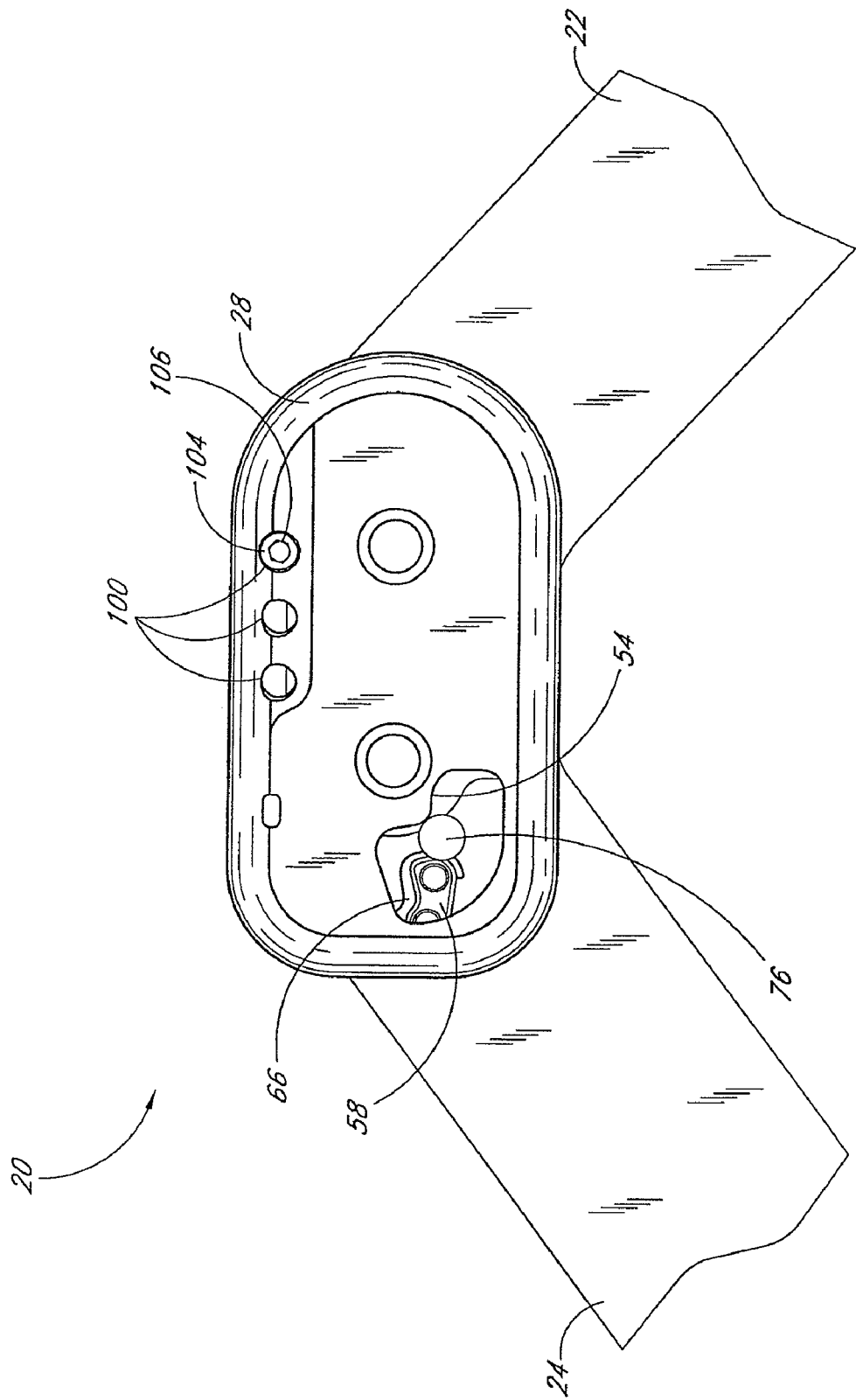
FIG. 15 is a top plan view of the hinge of FIG. 1, illustrating the easy accessibility of the adapter with the cosmetic cover removed.

The apertures 100 are adapted to receive a fulcrum 104, which in the illustrated embodiment comprises a shaft with an externally threaded head portion (FIG. 3). The head portion preferably includes a surface feature 106, such as a hexagonal depression, that is adapted to engage an adjustment tool, such as a hex key. The threaded portion of the fulcrum 104 engages the threads in one of the apertures 100 to secure the fulcrum 104 within that aperture, as shown in FIGS. 1 and 15. Thus, the fulcrum 104 is selectively positionable within one of the three apertures 100. When the fulcrum 104 is disposed in one of the apertures 100, the non-threaded portion of the shaft abuts the outermost leaf spring 80, as shown in FIG. 4. The position of the fulcrum 104 thus determines the bending characteristics of the leaf springs 80, as described below.

Those of skill in the art will appreciate that the fulcrum 104 could be retained within one of the apertures 100 using means other than a threaded engagement. For example, a friction fit could retain the fulcrum 104 within one of the apertures 100. However, a threaded engagement provides a wearer of a brace including the present hinge 20 with the advantageous ability to quickly remove the fulcrum 104 from a first aperture 100 and replace it in a different aperture 100. Thus, without disassembling the hinge, and without interchanging any parts of the hinge 20, the wearer can adjust the bending characteristics of the leaf springs 80, and thereby adjust a magnitude of the extension resistance felt by the wearer.

The mating end of each arm 22, 24 includes a first gear tooth 40 (FIG. 4) and additional gear teeth 108 (FIG. 3). The teeth 40, 108 on the first arm 22 interlock with the teeth 40, 108 on the second arm 24, such that the arms 22, 24 cannot pivot independently. As described above, the radial protrusion 44 from each reinforcing insert 38 comprises the first gear tooth 40 on each arm 22, 24. The harder material of the insert 38 reduces the amount of wear that the first gear teeth 40 experience, increasing the life span of the present hinge 20.

Figure 7:
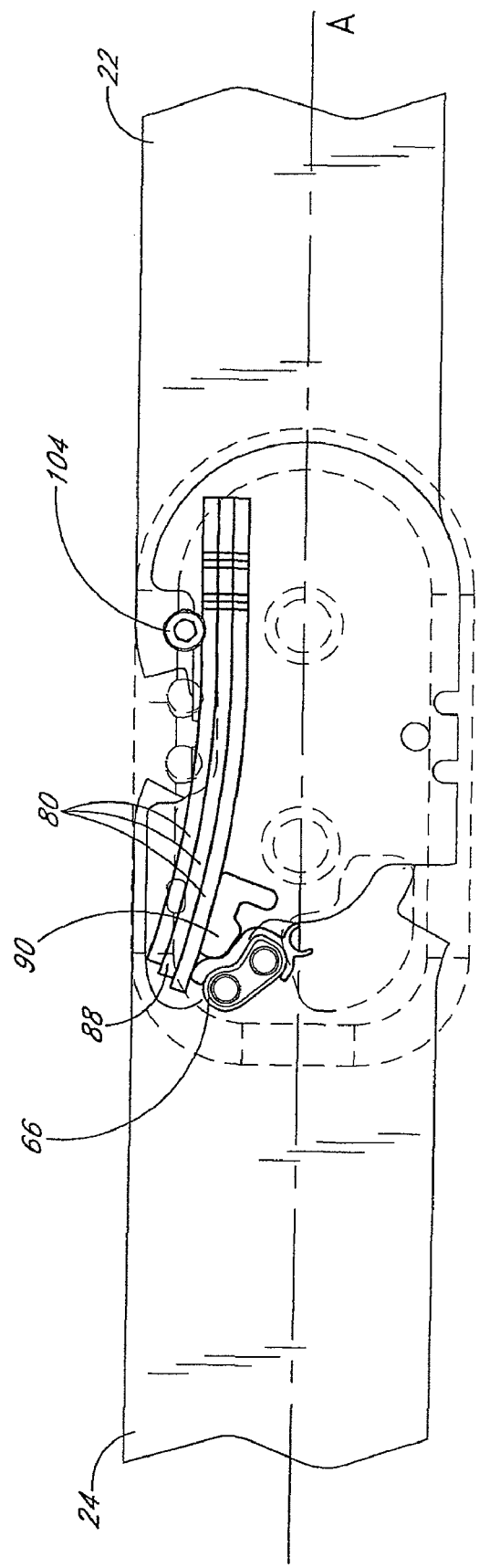
FIG. 7 is a top plan view of the components of FIG. 5, illustrating the configuration of these components when the arms are positioned at full extension, such that the springs are fully deflected, and the fulcrum is located at a maximum distance from the bumper.

As the arms 22, 24 pivot, the actuator 58 and adapter 66 move with the second arm 24. The arms 22, 24 are freely pivotable from a full flexion configuration (not shown) to a flexion angle at which the adapter 66 first contacts the bumper 90 (FIG. 5). As the arms 22, 24 pivot farther toward full extension (FIG. 7), the adapter 66 applies a force to the bumper 90, compressing the bumper 90 between the adapter 66 and the leaf springs 80. As the bumper 90 compresses, it in turn applies a force to the leaf springs 80, flexing the leaf springs 80 a small amount. Eventually, the bumper 90 compresses enough to allow the adapter 66 to contact the leaf springs 80, as shown in FIG. 7. The bumper 90 thus reduces any noise made when the adapter 66 contacts the leaf springs 80, because the leaf springs 80 are already flexing when the adapter 66 contacts the leaf springs 80. The adapter 66 and the bumper 90 then simultaneously apply force to the leaf springs 80, flexing the leaf springs 80 farther until they contact the wall 110 (FIGS. 9 and 10) of the outer hinge plate 28. In the illustrated embodiment, the hinge 20 reaches full extension as the leaf springs 80 contact the wall 110. Those of skill in the art will appreciate, however, that the leaf springs 80 may contact the wall 110 at any flexion angle.

Figure 6:
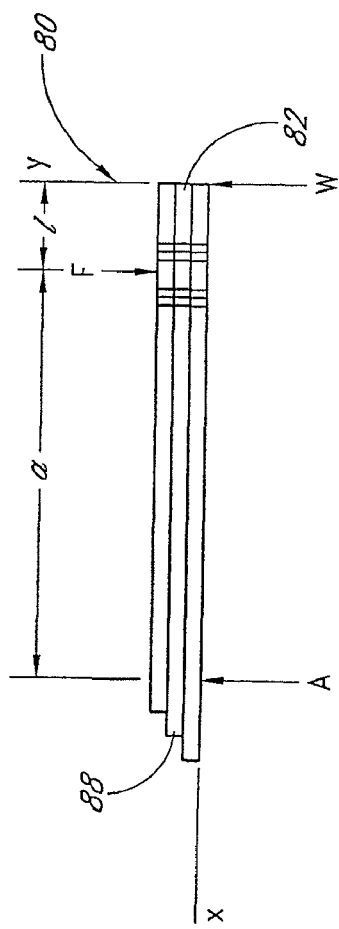
FIG. 6 is a top plan view of the springs of the hinge of FIG. 1, illustrating, schematically, the bending load applied to the springs by the hinge components.

The hinge assembly 20 thus places the leaf springs 80 in a three-point bending load, as illustrated in FIG. 6. The actuator 58/bumper 90 assembly applies a load A to the free ends 88 of the leaf springs 80 in a direction away from the axis A. The outer hinge plate first wall 84 (FIGS. 9 and 10) applies a load W to the fixed end 82 of the leaf springs 80 in a direction away from the axis A. The outer hinge plate second wall 86 or fulcrum 104 applies a load F to an intermediate portion of the leaf springs 80 in a direction toward the axis A. The location of the load F depends upon the position of the fulcrum 104, if the fulcrum 104 is inserted in one of the apertures 100. If the fulcrum 104 is absent, the outer hinge plate second wall 86 applies the force F.

The leaf springs 80 deflect as shown in FIG. 7 under the bending load. As the leaf springs 80 deflect from the configuration of FIG. 5 to that of FIG. 7, the force necessary to deflect the springs an incremental amount increases. Thus, a person wearing a knee brace including the hinge 20 experiences a steadily increasing resistive force as he or she extends his or her knee farther and farther. The hinge 20 thus provides a cushioned stop at full extension, and eliminates the uncomfortable jarring that could cause the problems outlined above.

Figure 11:
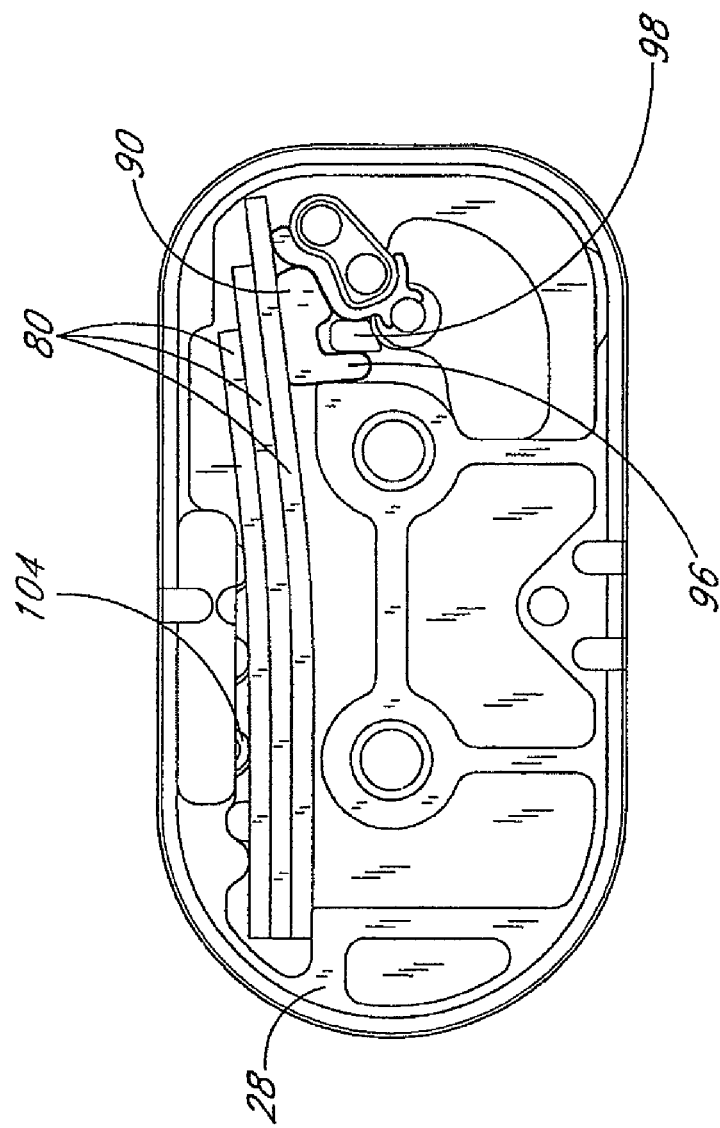
FIG. 11 is a bottom plan view of the actuator, adapter, bumper, springs, fulcrum and outer hinge plate of the hinge of FIG. 1, illustrating the configuration of these components when the arms are positioned at full extension, such that the springs are fully deflected, and the fulcrum is located at a maximum distance from the bumper.

When the wearer relaxes his or her leg, the leaf springs 80 urge the knee to flex until the leaf springs 80 return to their straight configuration, which is shown in FIGS. 5 and 10. As the hinge components move in this direction, the post 98 (FIG. 9) on the interior of the outer hinge plate 28 engages the base portion 96 of the bumper 90 and guides the bumper 90 back to its rest position, as shown in FIGS. 10 and 11.

The multiple positions for the fulcrum 104, and the removability of the fulcrum 104, enable the wearer, or a physician treating the wearer, to quickly adjust an amount of extension resistance experienced by the wearer without disassembling the hinge and without interchanging any parts of the hinge 20. With reference to FIG. 6, the properties of the leaf springs 80 can be determined using the well known model of a simply supported beam with an overhanging load. The deflection at the leaf spring free ends 88 is given by the following equation:

$$y_{FA} = \frac{A(x-l)}{6EI}[(x-l)^2 - a(3x-l)]$$

where
$y_{FA}$=deflection of the leaf springs 80 at any point between the applied load A and the reaction force F;
A=magnitude of the load applied by the actuator 58/adapter 66 to the leaf springs 80;
x=distance from the leaf spring fixed ends 82, as measured along the x-axis;
l=distance between the leaf spring fixed ends 82 and reaction force F applied by the hinge plate second wall 86 or fulcrum 104, as measured along the x-axis;
a=distance between the reaction force F applied by the hinge plate second wall 86 or fulcrum 104 and the load A applied by the actuator 58/adapter 66 to the leaf springs 80, as measured along the x-axis;
E=modulus of elasticity of the leaf springs 80 (a constant determined by the material used to construct the leaf springs 80); and
I=moment of inertia of the leaf springs 80 (a constant determined by the cross-sectional shape of the leaf springs 80).

To determine the deflection at the leaf spring free ends 88 (which is closely approximated by the deflection at the point of application of the applied load A), substitute (a+l) for x in the equation above. The equation then simplifies to:

$$y_{FA} = \frac{-Aa^2}{3EI}(a+l)$$

This equation illustrates that the deflection at the leaf spring free ends 88 is directly dependent upon both the magnitude of the load A applied by the actuator 58/adapter 66 to the leaf springs 80, and the distance a, which is the distance between the reaction force F applied by the hinge plate second wall 86 or fulcrum 104 and the applied load A. As one of these variables decreases, the other must increase in order to maintain a constant deflection of the leaf spring free ends 88. Thus, as the fulcrum 104 is moved toward the leaf spring free ends 88, thus decreasing the distance a, the applied load A must increase in order to maintain a constant deflection. In order for a wearer of a brace including the hinge 20 to extend his or her knee to a given flexion/extension angle, he or she will have to apply a greater force A as the fulcrum 104 moves toward the leaf spring free ends 88. In other words, the wearer experiences increasing extension resistance as the fulcrum 104 moves toward the leaf spring free ends 88. In a preferred embodiment, the hinge 20 provides a maximum of 14 in.-lbs. of resistance when the fulcrum 104 is located in the aperture 100 farthest from the leaf spring free ends 88, a maximum of 28 in.-lbs. of resistance when the fulcrum 104 is located in the intermediate aperture 100, and a maximum of 42 in.-lbs. of resistance when the fulcrum 104 is located in the aperture 100 closest to the leaf spring free ends 88.

Figure 8:
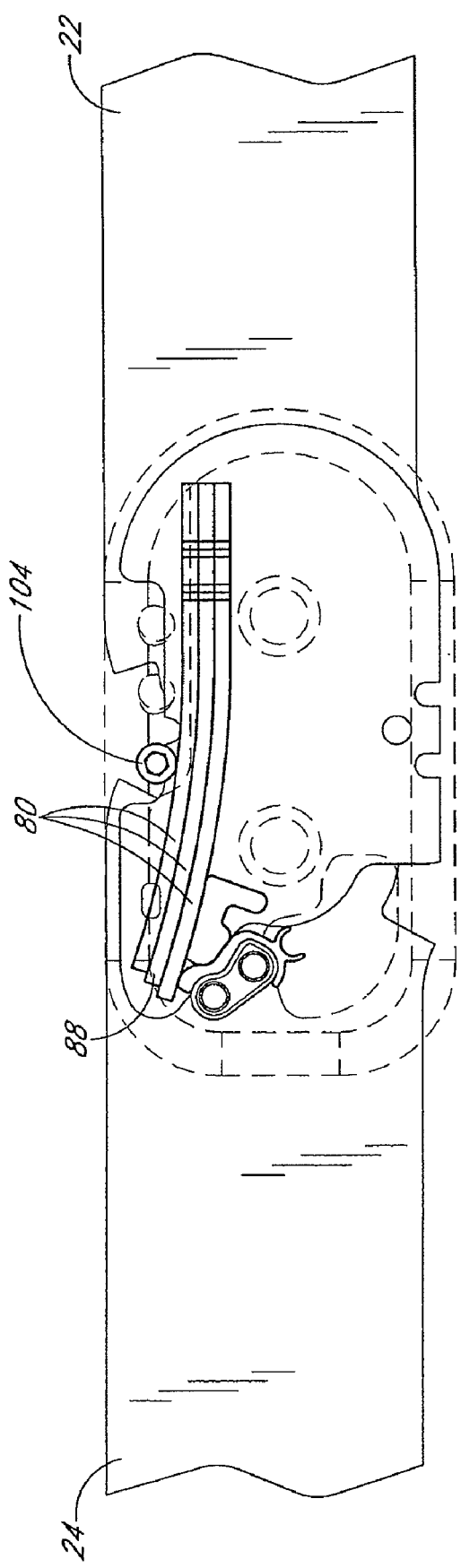
FIG. 8 is a top plan view of the components of FIG. 5, illustrating the configuration of these components when the arms are positioned at full extension, such that the springs are fully deflected, and the fulcrum is located at a minimum distance from the bumper.

With the fulcrum 104 removed (not shown), the wearer experiences very light extension resistance. With the fulcrum 104 positioned in the aperture 100 located a maximum distance from the free ends 88 of the leaf springs 80, as illustrated in FIGS. 5 and 7, the wearer experiences light extension resistance. With the fulcrum 104 positioned in the intermediate aperture 100, the wearer experiences an intermediate amount of extension resistance. With the fulcrum 104 positioned in the aperture 100 located a minimum distance from the free ends 88 of the leaf springs 80, as illustrated in FIG. 8, the wearer experiences heavy extension resistance. Those of skill in the art will appreciate that more apertures 100 could be provided in order to enable finer adjustment of the amount of extension resistance provided by the hinge 20. Those of skill in the art will further appreciate that the fulcrum 104 could be positionable along the leaf springs 80 using alternate apparatus. For example, the fulcrum 104 could comprise a portion of a switch (not shown) that is slidable along the outer hinge plate 28 and capable of being locked in place at a plurality of positions along the leaf springs 80.

The design of the present hinge 20 facilitates rapid removal and adjustment of the position of the fulcrum 104. As described above, the fulcrum 104 is alternately positionable in one of a plurality of apertures 100 in the outer hinge plate 28. To secure the fulcrum 104 within one of the apertures 100, the wearer inserts 38 the unthreaded shaft portion of the fulcrum 104 into one of the apertures 100 until the threads on the fulcrum 104 engage the threads within the aperture 100. Using an adjustment tool, such as a hex key, the wearer then rotates the fulcrum 104 within the aperture 100 until the fulcrum 104 is inserted a sufficient amount that it will not pop out of the aperture 100 during normal use of the hinge 20. Preferably, the wearer continues rotating the fulcrum 104 until it no longer protrudes from the outer surface 50 of the outer hinge plate 28. To move the fulcrum 104 to a different aperture 100, the wearer uses the adjustment tool to rotate the fulcrum 104 in the opposite direction, so that it withdraws from the aperture 100. The wearer then moves the fulcrum 104 to the desired aperture 100, and performs the insertion process just described.

The ability to quickly and easily move the fulcrum 104 from one aperture 100 to another enhances the versatility of a brace including the present hinge 20. For example, people of all different sizes and strengths may wear a brace including the present hinge 20. Wearers of great strength would likely benefit most from a brace having heavy extension resistance, while those of lesser strength would likely benefit most from a brace having light extension resistance. No matter the size and strength of the wearer, however, the present hinge 20 is quickly and easily adjustable to accommodate virtually any wearer. And the adjustment procedure does not require the wearer to disassemble the hinge or interchange any parts. Further, certain wearers may benefit from light extension resistance during an early phase of therapy, with the extension resistance steadily increasing as therapy progresses. Other wearers may benefit from heavy extension resistance during an early phase of therapy, with the extension resistance steadily decreasing as therapy progresses. The present hinge 20 enables such patients to undergo a course of therapy without having to change braces as therapy progresses.

Figure 12:
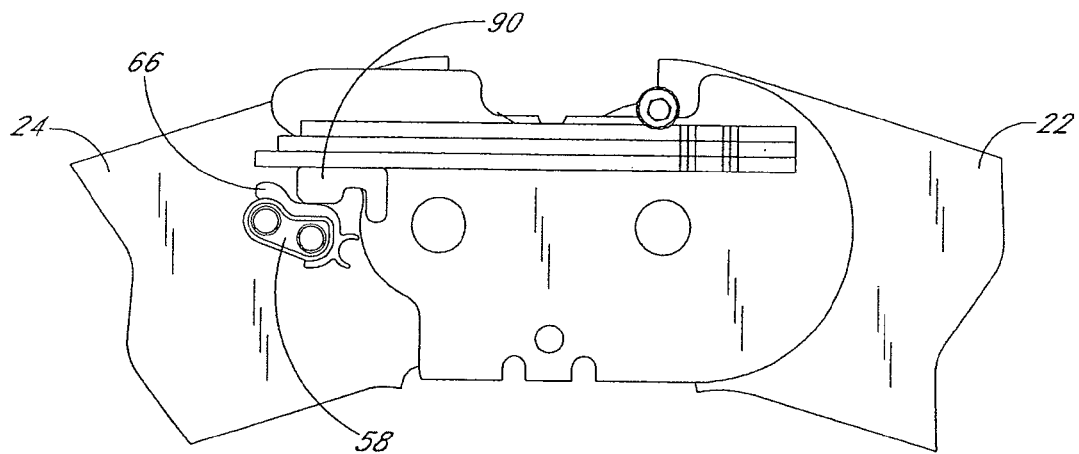
FIGS. 12-14 are top plan views of the actuator, adapter, bumper, springs, fulcrum, arms and friction plate of the hinge of FIG. 1, illustrating adapters of different sizes, and the relative configurations of these components when the arms are positioned such that the adapter contacts the bumper and the springs are undeflected.
Figure 13:
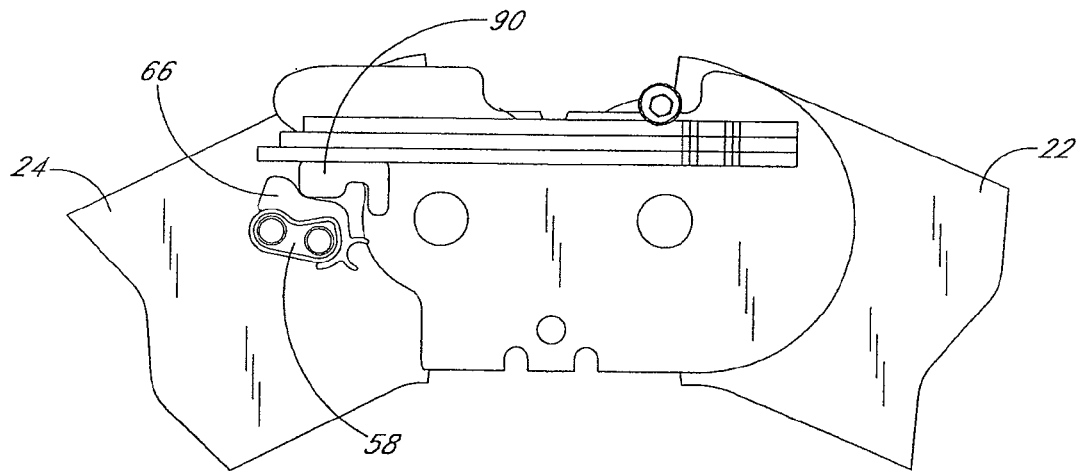
Figure 14:
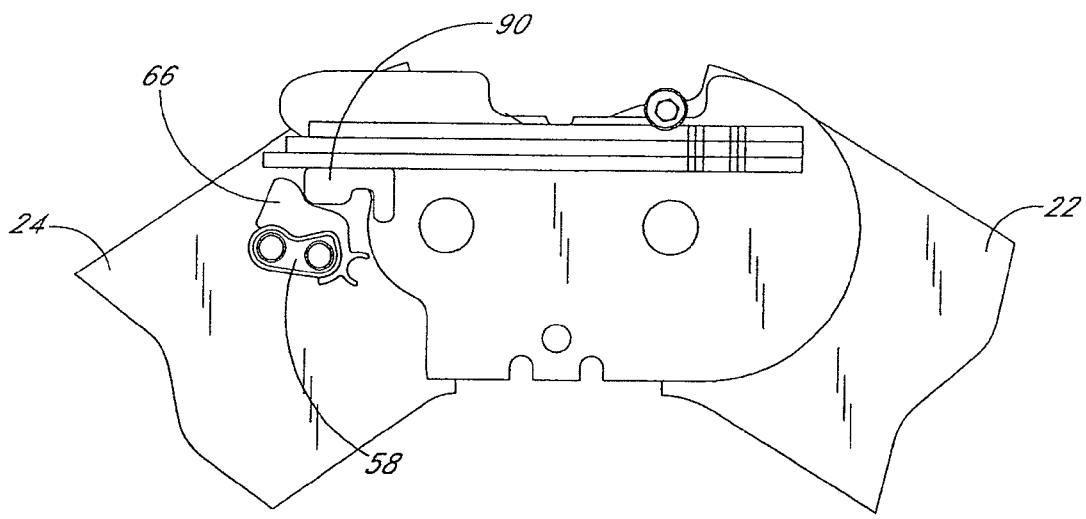

The hinge 20 enables easy adjustment of the flexion angle at which the wearer first experiences extension resistance. As shown in FIGS. 12-14, the wearer may place adapters 66 of various sizes on the actuator 58. In FIG. 12, a relatively small adapter 66 is positioned on the actuator 58. The adapter 66 first contacts the bumper 90 at a flexion angle of approximately 35°, and the wearer first experiences extension resistance at this same angle. In FIG. 13, a slightly larger adapter 66 is positioned on the actuator 58. The adapter 66 first contacts the bumper 90 at a flexion angle of approximately 45°, and the wearer first experiences extension resistance at this same angle. Finally, in FIG. 14, an even larger adapter 66 is positioned on the actuator 58. The adapter 66 first contacts the bumper 90 at a flexion angle of approximately 55°, and the wearer first experiences extension resistance at this same angle. Those of skill in the art will appreciate that adapters 66 of virtually any size may be positioned on the actuator 58 so that the wearer first experiences extension resistance at virtually any flexion angle. Those of skill in the art will appreciate that the adapter 66 could be completely removed in order to further decrease the flexion angle at which the wearer first experiences extension resistance.

As described above, the adapter 66 is secured in place with the retaining member 76 (FIGS. 15 and 16). To exchange one adapter 66 for another of a different size, the wearer first removes the cosmetic cover 52, if one is provided, from the outer hinge plate 28. The wearer can then access the adapter 66 through the adapter access opening 54 in the outer hinge plate 28. The wearer removes the retaining member 76 using an appropriate tool, such as a screwdriver or a hex key. The wearer can then remove the adapter 66 from the actuator 58 using his or her fingers or a tweezers, and replace the adapter 66 with one of a different size. To secure the adapter 66 in place, the wearer replaces the retaining member 76. Finally, the wearer replaces the cosmetic cover 52, if one is provided.

The present hinge 20 has been described above as a hinge for providing resistance to joint extension. Those of skill in the art will appreciate that the configuration of the present hinge 20 could easily be adapted to enable the hinge 20 to provide resistance to joint flexion. For example, if the leaf springs 80 were housed within the outer hinge plate 28 such that they were lay adjacent a rear edge of the outer hinge plate 28, then the actuator 58/adapter 66 assembly would approach and contact the leaf springs 80 as a flexion angle between the arms 22, 24 increased.

The present hinge 20 has also primarily been described above as a hinge for use with a knee brace. Those of skill in the art will appreciate that the present hinge 20 is adapted for use in a brace that is worn about any body joint.

SCOPE OF THE INVENTION

The above presents a description of the best mode contemplated for carrying out the present motion controlling hinge for orthopedic brace, and of the manner and process of making and using it, in such full, clear, concise, and exact terms as to enable any person skilled in the art to which it pertains to make and use this hinge. This hinge is, however, susceptible to modifications and alternate constructions from that discussed above that are fully equivalent. Consequently, this hinge is not limited to the particular embodiments disclosed. On the contrary, this hinge covers all modifications and alternate constructions coming within the spirit and scope of the hinge as generally expressed by the following claims, which particularly point out and distinctly claim the subject matter of the hinge.

What is claimed is:

1. A hinge for an orthopedic brace, comprising:
   a hinge plate;
   a first arm pivotably secured to the hinge plate;
   a second arm pivotably secured to the hinge plate;
   an actuator secured to the second arm; and
   a spring member; wherein
   as the arms pivot in a flexion direction such that an angle between them increases, once the arms reach a desired flexion angle, the spring member exerts a force on the actuator tending to bias the second arm in an extension direction opposite the flexion direction.

2. The hinge of claim 1, wherein the spring member comprises at least one flat bar.

3. The hinge of claim 2, wherein the spring member comprises three flat bars.

4. The hinge of claim 3, wherein the hinge plate supports a fixed end of the spring member, restraining the fixed end against translation along a first axis.

5. The hinge of claim 4, wherein as the arms pivot in the flexion direction, the actuator contacts a free end of the spring member, flexing the spring member.

6. The hinge of claim 5, further comprising a fulcrum located intermediate the fixed end and the free end of the spring member.

7. The hinge of claim 6, wherein the fulcrum, together with the hinge plate and the actuator, creates a three-point bending load on the spring member.

8. The hinge of claim 6, wherein the fulcrum is selectively positionable at a plurality of locations along the spring member.

9. The hinge of claim 8, wherein the hinge plate includes at least one aperture.

10. The hinge of claim 9, wherein the at least one aperture is adapted to receive the fulcrum.

11. The hinge of claim 9, wherein the at least one aperture includes internal threads.

12. The hinge of claim 11, wherein the fulcrum comprises a shaft including external threads, and the external threads engage the internal threads in the at least one aperture to secure the fulcrum within the aperture.

13. The hinge of claim 1, further comprising an adapter secured to the actuator.

14. The hinge of claim 13, wherein the adapter is positioned between the actuator and the spring member, such that the thickness of the adapter determines an angular position of the second arm at which the spring member first exerts force on the actuator.

15. The hinge of claim 14, further comprising a bumper positioned between the actuator and the spring member.

16. The hinge of claim 15, wherein as the arms pivot in the flexion direction, the adapter contacts the bumper, which in turn contacts the spring member, causing the spring member to flex.

17. The hinge of claim 1, wherein the hinge plate is a first hinge plate, and the hinge further comprises a second hinge plate spaced from the first hinge plate such that the arms are located between the first and second hinge plates.

18. An orthopedic brace including a hinge, the hinge comprising:
   a hinge plate;
   a first arm pivotably secured to the hinge plate;
   a second arm pivotably secured to the hinge plate;
   an actuator secured to the second arm; and
   a spring member; wherein
   as the brace pivots toward full flexion, the spring member exerts a force on the actuator tending to bias the brace away from full flexion.

19. A method of adjusting a magnitude of a resistive force provided by a hinge, the method comprising the steps of:
   removing a fulcrum from a first aperture of a hinge plate of the hinge;
   translating the fulcrum along the hinge plate to a second aperture of the hinge plate; and
   securing the fulcrum within the second aperture;
   wherein the hinge moves freely through a preset flexion/extension range until the hinge reaches a preset flexion angle, $\theta$, and in a range between $\theta$ and a maximum flexion angle of the hinge, the hinge resists further flexion with a resistive force that increases as the hinge moves from $\theta$ to the maximum flexion angle, and when the fulcrum is disposed in the first aperture the resistive force provided by the hinge lies within a first range, and when the fulcrum is disposed in the second aperture the resistive force provided by the hinge lies within a second range.

20. The method of claim 19, wherein the step of translating the fulcrum changes a position of the fulcrum relative to at least one leaf spring associated with the hinge plate.

* * * * *